United States Patent [19]

Yang

[11] Patent Number: 5,336,741
[45] Date of Patent: Aug. 9, 1994

[54] FLUORINATED POLYMER AND MONOMERS

[75] Inventor: Zhen-Yu Yang, Wilmington, Del.

[73] Assignee: E. I. Du Pont de Nemours and Company, Wilmington, Del.

[21] Appl. No.: 169,917

[22] Filed: Dec. 20, 1993

[51] Int. Cl.$^5$ .............................................. C08F 16/24
[52] U.S. Cl. .................................. 526/247; 524/113; 524/233; 524/315; 524/365; 428/76
[58] Field of Search ................ 526/247; 524/113, 315, 524/233, 365; 428/76

[56] References Cited

U.S. PATENT DOCUMENTS 4,897,457  1/1990  Nakamura et al. .
5,260,492  11/1993  Feiring et al. .

OTHER PUBLICATIONS

Fearn, J. E. et al, J. Polym. Sci. A-1, 4, 131-140, 1966.
Brown, D. W. et al, J. Polym. Sci. A-2, 7, 601-608, 1969.

Primary Examiner—Joseph L. Schofer
Assistant Examiner—N. Sarofim

[57] ABSTRACT

Disclosed herein is a partially fluorinated polymer containing cyclic units. The polymer is particularly useful in for coatings and encapsulants. Also disclosed herein is the novel monomer from which the polymer is made, and a novel intermediate for that monomer.

8 Claims, No Drawings

FLUORINATED POLYMER AND MONOMERS

FIELD OF THE INVENTION

This invention concerns a novel partially fluorinated alkenyl vinyl ether which can be (co)polymerized to novel polymers containing ring structures. The polymers are useful for films and coatings. Also claimed is a novel intermediate for making the monomer.

TECHNICAL BACKGROUND

The instant monomer, a partially fluorinated omega-alkenyl vinyl ether, can be polymerized to an uncrosslinked (soluble), amorphous polymer.

U.S. Pat. No. 4,897,457 reports that perfluorinated omega-alkenyl vinyl ethers can be polymerized to polymers that are amorphous and contain ring structures.

J. E. Fearn, et al., J. Polym. Sci. A-1, volume 4, p. 131–140 (1966) and D. W. Brown et al., J. Polym. Sci. A-2, vol. 7, p. 601–608 (1969) indicate that certain perfluorinated alpha-omega dienes can be polymerized to soluble ring containing polymers. These polymers are not reported to be crystalline.

U.S. Pat. No. 5,260,492 describes polymers, from partially fluorinated omega-alkenyl vinyl ethers, which polymers contain cyclic structure(s). The polymers are reported to be uncrosslinked and crystalline.

SUMMARY OF THE INVENTION

This invention concerns a polymer, comprising, the repeat unit

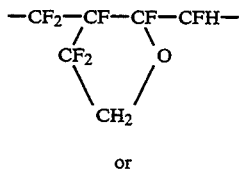

or

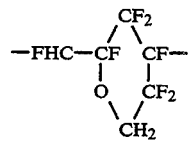

or both.

This invention also concerns a compound of the formula $R^1CF_2CH_2OCF=CFH$, wherein $R^1$ is $CF_2ClCFCl-$ or $CF_2=CF-$.

DETAILS OF THE INVENTION

This invention concerns a certain partially fluorinated omega-alkenyl vinyl ether and a polymer made by free radical polymerization from that vinyl ether. The polymer is totally amorphous and is useful where transparency and low light scattering are important, such as jacketing for an optical fiber. The polymer is soluble in common organic solvents, and is therefore particularly suited for films and coatings.

The syntheses of the omega-alkenyl vinyl ether, and its dichloro precursor are found in Examples 1 and 2.

The free radical (co)polymerization of the fluorinated omega-alkenyl vinyl ether can be done by conventional means known to those skilled in the art of fluoroolefin (including vinyl ethers)polymerization, see U.S. Pat. No. 4,897,457 and H. F. Mark, et al., Ed., Encyclopedia of Polymer Science and Engineering, Vol. 16, John Wiley and Sons, New York, 1989, p. 577–648, both of which are hereby included by reference. The polymerization can be carried out neat, in solvent, or in nonaqueous suspension, aqueous suspension, or aqueous emulsion. Typical suitable free radical initiators include bis(perfluoropropionyl) peroxide and bis (4-t-butylcyclohexylperoxy) dicarbonate. Typical (co)polymerizations are described in Examples 3 and 4.

Suitable comonomers include fluorinated and unfluorinated monomers such as tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, perfluoro(2,2-dimethyl-1,3-dioxole), and $CF_2=CF(CF_2)_mOCF=CF_2$ where m is 1, 2 or 3. Preferred comonomers are tetrafluoroethylene and perfluoro(propyl vinyl ether). Also preferred is the homopolymer of the instant fluorinated omega-alkenyl vinyl ether.

By "comprising" herein, in the claim to polymers containing the

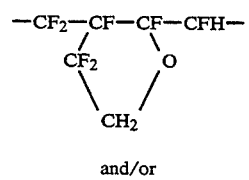

and/or

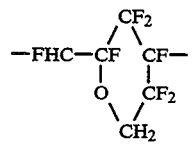

repeat units, is meant that the polymer contains these unit(s), and can optionally contain other units (from comonomers) so as to form a copolymer.

The polymers made herein are useful in molding parts, and in coatings and encapsulants. They are particularly useful as coatings and encapsulants because even though they may have a high fluorine content and good thermal stability, they are soluble in organic solvents, such as ethyl acetate, acetone, tetrahydrofuran and N,N-dimethylformamide. Solutions of the polymers may be used to coat or encapsulate articles in conventional ways.

In the Examples, the following abbreviations are used:

DMF—N,N-dimethylformamide
GC—gas chromatography
GPC—gel permeation chromatography
Mn—number average molecular weight
Mw—weight average molecular weight
TGA—thermogravimetric analysis

EXAMPLE 1

Preparation of $CF_2ClCFClCF_2CH_2OCF=CFH$

To a stirred solution of 9.0 g (60% dispersion in mineral oil) of NaH and 150 mL of ether was slowly added 30 g of 3,4-dichloro-2,2,3,4,4-pentafluorobutanol at 0° C. After the addition was complete, the reaction mixture was stirred at room temperature for 3 hours, and then transferred into a 0.4 L shaker tube. The tube was purged with $N_2$ and pressured with 100 g of trifluoroethylene and then kept at 50° C. for 50 hours. The reaction mixture was quenched with 10 mL of methanol and poured into 50 mL of water. The ether layer was separated and aqueous layer was extracted with ether. The combined ether layers were dried over MgSO$_4$. After evaporation of the ether, the residue was distilled under reduced pressure to give 20.4 g of material, bp 69°–71° C./40 mmHg. GC and NMR indicated that the product is an E/Z isomeric mixture in a 3:1 ratio and contained 30% of starting alcohol. $^1$H NMR: 6.70 (dd, J=72.9 Hz, J=3.9 Hz, E), 6.50 (dd, J=72.9 Hz, J=13.7 Hz, Z) [total 1H], 4.54 (t, J=13.7 Hz, E), 4.41 (t, J=13.6 Hz, Z), [total 2H]. $^{19}$F NMR: −63.5 to −64.7 (m, 2F), −114.0 to −115.0 (m, 2F), −106.3 (t, J=14.8 Hz, Z), −131.7 (d, J=121.0, E), [total 1F], −131.8 (m, 1F), −189.6 (dd, J=71.2 Hz, J=15.7 Hz, Z), −196.5 (dd, J=121.3 Hz, J=73.0 Hz, E) [total 1F]. HRMS: Calcd. for (C$_6$H$_3$F$_7$Cl$_2$O+H): 294.9527. Found: 294.9514.

EXAMPLE 2

Preparation of CF$_2$=CFCF$_2$CH$_2$OCF=CFH

To a stirred solution of 6.5 g of Zn and 15 mL of DMF was added 0.5 mL of 1,2-dibromoethylene at 90° C. After the resulting mixture was stirred for 20 minutes, 18.0 g of above difluorovinyl ether (Example 1) was slowly added over 30 minutes at 100° C. After the addition was complete, the reaction mixture was stirred for 1.5 hours. Volatile materials (7.5 g) were collected in dry ice-acetone trap under partial vacuum (200–130 mmHg). Redistillation gave 5.2 g of desired product as an E/Z isomeric mixture in a 3.0:1 ratio, bp 60°–63° C./210 ramrig, 99.8% purity. $^1$H NMR: 6.68 (dd, J=73 Hz, J=4.0 Hz, E), 6.46 (dd, J=73 Hz, J=13.7 Hz), [total 1H], 4.37 (t, J=11.2 Hz, E), 4.25 (t, J=11.5 Hz, Z), [total 2H]. $^{19}$F NMR: −92.1 and −92.2 (ddt, J=58.3 Hz, J=36.5 Hz, J=5.5 Hz, 1F), −107.5 to −108.5 (m, 1.33F), −111.4 (m, 2F), −131.3 (dd, J=121.9 Hz, J=4.0 Hz, 0.66F), −189.7 to −190.5 (m, 1.33F), −196.7 (dd, J=121.9 Hz, J=73 Hz, 0.66F). IR: 3140 (w), 2960 (w), 1790 (s), 1750 (s), 1315 (s), 1170 (s), 1145 (s), 1065 (s), 1035 (s).

EXAMPLE 3

Homopolymerization of CF$_2$=CFCF$_2$CH$_2$OCF=CFH

A 25 mL glass ampul fitted with a Teflon ® coated stir bar was charged with 0.2 mL of 5% of bis(perfluoropropionyl)peroxide in 1,1,2-trichlorotrifluoroethane and 1.2 g of the title compound. The ampul was sealed and cooled in a liquid nitrogen bath. After being evacuated and purged with N$_2$ alternately six times, contents of the sealed ampul were stirred at 35°–40° C. for 24 hours. The resulting white solids were dissolved in ethyl acetate, reprecipitated by addition of methanol containing 10% water and dried under vacuum at 100° C. to give 0.54 g of polymer.

The IR spectrum of this polymer showed no absorption at around 1790 and 1750 cm$^{-1}$ which could be attributed to double bonds in the polymer. 1H NMR and $^{19}$F NMR analysis of this polymer in acetone-d$_6$ indicated the cyclic structure. IR: 2980 (w), 1470 (w), 1380 (m), 1280 (s), 1250 (s), 1120 to 1140 (s) . $^1$H NMR (vs. TMS): 5.4 to 5.8 (br, $^1$H), 4.8 (br, 2H); $^{19}$F NMR (vs. CFCl$_3$): −110.8 to −121.6 (m, 7F), −179 to −180.5 (m, 1F), −205 (m, 1F).

This polymer was soluble in acetone, ethyl acetate, tetrahydrofuran and DMF, and was insoluble in 1,1,2-trichlorotrifluoroethane, chloroform, toluene, and methanol. The polymer had a glass transition temperature of 134°–141° C. It could be obtained as a colorless and transparent thin film upon removing solvent from its solution in DMF spread on a glass plate. GPC analysis indicated that M$_w$ was 2.2×10$^5$ and M$_n$ was 1.27×10$^4$. By TGA the polymer showed 10% weight loss temperatures of about 445° C. in nitrogen and 335° C. in air, respectively, when heated at 20° C./minute.

EXAMPLE 4

Copolymerization of CF$_2$=CFCF$_2$CH$_2$OCF=CFH with perfluoropropylvinyl ether (PPVE)

A 25 mL glass ampul fitted with a Teflon ® coated stir bar was charged with 0.2 mL of 5% of bis(perfluoropropionyl) peroxide in 1,1,2-trichlorotrifluoroethane, 1.0 g of CF$_2$=CFCF$_2$CH$_2$OCF=CFH and 1.0 g of PPVE. The ampul was sealed and cooled in a liquid nitrogen bath. After being evacuated and purged with N$_2$ gas six times, contents of the sealed ampul were stirred at 40° C. for 24 hours. The resulting white solids were dissolved in ethyl acetate, reprecipitated by addition of methanol containing 10% water and dried under vacuum at 100° C. to give 0.81 g of polymer. This polymer was dissolved in acetone-d$_6$ to measure its $^{19}$F NMR spectrum, from which the polymer was found to be a copolymer consisting of a unit of the cyclic structure derived from CF$_2$=CFCF$_2$CH$_2$OCF=CFH and a unit of the structure derived from PPVE in a 94.3 to 5.7 ratio. $^1$H NMR: 5.8 to 5.4 (br, 1H), 4.8 (br, 2H). 19F NMR: −81.0 (m, CF$_3$), −109 to −121.6 (m, CF$_2$ and CFO), −129.0 (s, CF$_2$ of PPVE), −179 to −180.5 (m, CF), −203 to −205 (m, CFH).

The polymer had a glass transition temperature of 128° to 135° C. GPC analysis indicated that Mw was 2.84×10$^5$ and Mn was 1.84×10$^4$. By TGA the polymer showed 10% weight loss temperatures of about 460° C. in nitrogen and 355° C. in air, respectively, when heated at 20° C./minute.

What is claimed is:

1. A polymer, comprising, the repeat unit

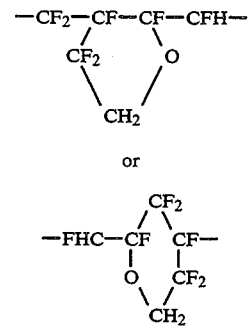

or both, provided that the polymer is totally amorphous.

2. The polymer of claim 1 which is a homopolymer.

3. The polymer of claim 1 which is a copolymer.

4. The polymer of claim 3 wherein a comonomer is one or more of tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, perfluoro(2,2-dimethyl-I, 3-dioxole), or CF$_2$=CF (CF$_2$)$_m$OCF=CF$_2$ where m is 1, 2 or 3.

5. The polymer of claim 4 wherein said comonomer is tetrafluoroethylene or perfluoro(propyl vinyl ether).

6. A solution of the polymer of claim 1 in a solvent.

7. The solution of claim 6 wherein the solvent is selected from the group consisting of ethyl acetate, acetone, tetrahydrofuran and N,N-dimethylformamide.

8. An article encapsulated with the polymer of claim 1.

* * * * *